(12) United States Patent
Kim et al.

(10) Patent No.: US 8,691,794 B2
(45) Date of Patent: Apr. 8, 2014

(54) TOPICAL COMPOSITION FOR SKIN CONTAINING POLYSACCHARIDE EXTRACT OF RED GINSENG

(75) Inventors: Ji Seong Kim, Yongin-si (KR); Myeong Hun Yeom, Yongin-si (KR); Sun Sang Kwon, Yongin-si (KR); Duck Hee Kim, Seoul (KR); Han Kon Kim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 13/504,682

(22) PCT Filed: Nov. 23, 2010

(86) PCT No.: PCT/KR2010/008272
§ 371 (c)(1),
(2), (4) Date: Apr. 27, 2012

(87) PCT Pub. No.: WO2011/065719
PCT Pub. Date: Jun. 3, 2011

(65) Prior Publication Data
US 2012/0238743 A1 Sep. 20, 2012

(30) Foreign Application Priority Data
Nov. 30, 2009 (KR) .................. 10-2009-0116466

(51) Int. Cl.
*A01N 43/04* (2006.01)
*A61K 31/715* (2006.01)

(52) U.S. Cl.
USPC .......................................... 514/54

(58) Field of Classification Search
None
See application file for complete search history.

(56) References Cited

U.S. PATENT DOCUMENTS

| | | | |
|---|---|---|---|
| 6,083,932 A * | 7/2000 | Pang et al. | 514/54 |
| 6,899,902 B1 * | 5/2005 | Hwang | 424/728 |
| 2008/0045467 A1 | 2/2008 | Kim et al. | |
| 2010/0310485 A1 | 12/2010 | Park et al. | |

FOREIGN PATENT DOCUMENTS

| | | |
|---|---|---|
| CN | 1909885 | 2/2007 |
| CN | 101143155 | 3/2008 |
| CN | 101239030 | 8/2008 |
| CN | 101820854 | 9/2010 |
| KR | 10-2005-0068196 | 7/2005 |
| KR | 10-2006-0109798 | 10/2006 |

OTHER PUBLICATIONS

International Search Report for PCT/KR2010/008272, mailed Aug. 31, 2011.
KR Language Written Opinion of the International Searching Authority for PCT/KR2010/008272, mailed Aug. 31, 2011.
Chepurnov, S.A. et al., "The Central Effects of Saponin Components and Polysaccharides Fraction from Korean Red Ginseng", Korean J. Ginseng Sci., vol. 18, No. 3, pp. 165-174, (1994).
Lee, C.K. et al., "Biological Activity of Acidic Polysaccharide of Korean Red Ginseng I.-Effects on Alcohol Detoxification System in the Liver of Alcohol-intoxicated Rats", J. Ginseng Res., vol. 22, No. 4, pp. 260-266, (1998).
Int'l Search Report for PCT/KR2010/008272, two pages, mailed Aug. 31, 2011.
Written Opinion for PCT/KR2010/008272, four pages, mailed Aug. 31, 2011.
Office Action for counterpart Chinese Application 201080052447.3, six pages, mailed Jan. 5, 2013.

* cited by examiner

*Primary Examiner* — Layla Bland
(74) *Attorney, Agent, or Firm* — Nixon & Vanderhye PC

(57) ABSTRACT

The present invention relates to a composition for skin application, which has the effects of reducing skin wrinkles, enhancing skin elasticity and preventing skin aging, and more particularly, to a composition for skin application, which contains, as an active ingredient, a polysaccharide extract of red ginseng having a molecular weight of less than 10,000, in which the polysaccharide extract of red ginseng has the effect of increasing the expression of mitochondrial electron transport system enzymes in human skin keratinocytes to enhance the activity of the skin cells, thereby reducing skin wrinkles, increasing skin elasticity and preventing skin aging.

6 Claims, 4 Drawing Sheets

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
agccctcgct gtcactttcc tagga                                              25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tgaaagagta tgatggggtg gtggt                                              25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
attactgcag gccacctact catgc                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
cgtatggccc accataatta ccccc                                              25

TOPICAL COMPOSITION FOR SKIN CONTAINING POLYSACCHARIDE EXTRACT OF RED GINSENG

This application is the U.S. national phase of International Application No. PCT/KR2010/008272, filed 23 Nov. 2010, which designated the U.S. and claims priority to Korea Application No. 10-2009-0116466, filed 30 Nov. 2009, the entire contents of each of which are hereby incorporated by reference.

SEQUENCE LISTING

The instant application contains a Sequence Listing which has been submitted in ASCII format via EFS-Web and is hereby incorporated by reference in its entirety. Said ASCII copy, created on May 21, 2012, is named 91296.txt and is 1,339 bytes in size.

TECHNICAL FIELD

The present invention relates to a composition for skin application, which has the effects of reducing skin wrinkles, enhancing skin elasticity and preventing skin aging, and more particularly, to a composition for skin application, which contains, as an active ingredient, a polysaccharide extract of red ginseng having a molecular weight of less than 10,000, in which the polysaccharide extract of red ginseng has the effect of increasing the expression of mitochondrial electron transport system enzymes in human skin keratinocytes to enhance the activity of the skin cells, thereby reducing skin wrinkles, increasing skin elasticity and preventing skin aging.

BACKGROUND ART

Intracellular mitochondria synthesize the energy storage molecule ATP in cells using the chemical energy of nutrients through the electron transport system. Enzymes which play an important role in this electron transport system are electron transport system enzymes. When the chemical energy of nutrients is transferred to electrons, high-energy electrons are generated and transported between several enzymes of the electron transport system while the energy of the electrons is released. The released energy is used to form a proton gradient which is used to synthesize ATP. Mitochondria transport protons using the energy of electrons and make the concentration of protons different across the inner membrane. This difference in concentration is called a "proton gradient". When the proton channel of the inner membrane is open in the state in which the concentration of protons differs between the inside and the outside of the inner membrane, protons flow from an area of high proton concentration to an area of low proton concentration, and the energy of this flow is used to synthesize ATP.

The mitochondrial inner membrane (cristae) includes numerous electron transport system enzymes. When electrons are transported between these electron transport system enzymes, the energy of the electrons is consumed and protons are transported out of the mitochondrial inner membrane. Enzymes located in the mitochondrial inner membrane and the functions thereof will now be described in further detail. The first electron transport enzyme is flavin mononucleotide (FMN). It is an enzyme attached to the mitochondrial inner membrane and receives two electrons and two protons from NADH that is the product of the dehydrogenase reaction. Favin mononucleotide transports the two protons, received from NADH, to the outside of the inner membrane, and transfers the two electrons to coenzyme Q (CoQ) which is the next enzyme of the electron transport system. The coenzyme Q that received the electrons binds to two protons in the inner membrane to form $CoQH_2$, and then transport the two protons out of the inner membrane. At the same time, the two electrons received in the coenzyme are transferred to cytochrome b. The electrons transferred to cytochrome b are transferred sequentially to cytochrome c1, cuytochrome c, cytochrome a, and finally to cytochrome a3 in which the electrons are transferred to oxygen to form water. The protons transported in this process form a proton gradient across the mitochondrial inner membrane.

The electron transport is composed of four different complexes: complex I (NADH: ubiquinone oxidoreductase), complex II (succinate: ubiquinone oxidoreductase), complex III (ubiquinol: cytochrome C oxidoreductase), and complex IV (cytochrome C: oxidoreductase). In the process in which electrons are transferred from complex I through complex IV to an oxygen molecule, hydrogen ions are pumped out of the mitochondrial matrix while a membrane potential is formed. When hydrogen ions flow into the mitochondrial matrix by F0/F1-ATP synthase (complex V), ATP is produced from ADP. This process is referred to as oxidative phosphorylation (OXPHOS).

DISCLOSURE

Technical Problem

The present inventors have found that, among polysaccharide extracts of red ginseng, a polysaccharide extract having a molecular weight of less than 10,000 has the effect of increasing the expression of mitochondrial electron transport system enzymes in human skin keratinocytes to increase the activity of the skin cells, thereby showing the effects of reducing skin wrinkles, enhancing skin elasticity and preventing skin aging. Based on this finding, the present invention has been completed.

Therefore, it is an object of the present invention to provide a composition for skin application for reducing skin wrinkles, enhancing skin elasticity and preventing skin aging.

Technical Solution

In order to accomplish the above objects, the present invention provides a composition for skin application, which contains, as an active ingredient, a polysaccharide extract of red ginseng having a molecular weight of less than 10,000.

Advantageous Effects

The inventive polysaccharide extract of red ginseng having a molecular weight of less than 10,000 can increase the expression of cell transport system enzymes in human skin keratinocytes, compared to a polysaccharide extract of white ginseng having the same molecular weight and polysaccharide extracts of red ginseng having other molecular weights. Thus, the inventive polysaccharide extract of red ginseng can increase the energy activity of the skin keratinocytes, thereby showing the effects of promoting skin regeneration, enhancing skin activity, enhancing skin elasticity, preventing skin aging and improving complexion.

BEST MODE

Figure 1:
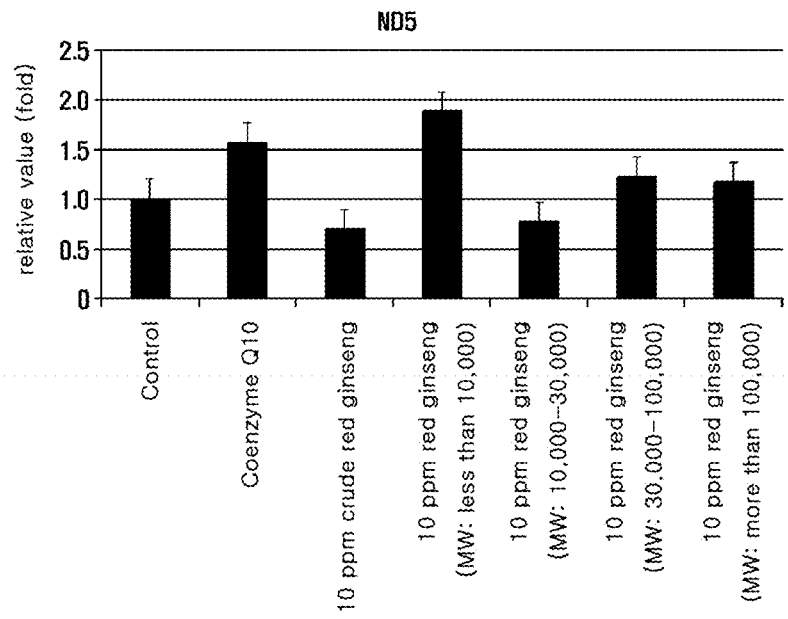
FIGS. 1 to 4 are graphic diagrams showing the results obtained by fractionating polysaccharide extracts of red ginseng according to molecular weight, performing RT-PCR for the expression of the mitochondrial enzymes ND5, ND6, ATP6 and ATP8, and then measuring the ratios of the expressions of the mitochondrial enzymes in those in a control.

The present invention relates to a composition for skin application, which contains, as an active ingredient, a polysaccharide extract of red ginseng having a molecular weight of less than 10,000.

The present invention also relates to a composition for skin application for promoting the expression of mitochondrial electron transport system enzymes in skin cells, the composition containing, as an active ingredient, a polysaccharide extract of red ginseng having a molecular weight of less than 10,000.

Moreover, the present invention relates to a composition for skin application for reducing skin wrinkles, the composition containing, as an active ingredient, a polysaccharide extract of red ginseng having a molecular weight of less than 10,000.

Furthermore, the present invention relates to a composition for enhancing skin elasticity, the composition containing, as an active ingredient, a polysaccharide extract of red ginseng having a molecular weight of less than 10,000.

In addition, the present invention relates to a composition for preventing skin aging, the composition containing, as an active ingredient, a polysaccharide extract of red ginseng having a molecular weight of less than 10,000.

Hereinafter, the present invention will be described in further detail.

As used herein, the term "extract" is meant to include all materials obtained by extracting components from natural materials by any method. Examples of the extract include solvent-soluble components extracted from natural materials using water or organic solvents, and materials obtained by extracting specific components (e.g., oil) from natural materials.

As used herein, the term "skin" is meant to include not only a tissue covering the surface of the face or body of an animal, but also scalp and hair.

Red ginseng which is used in the present invention is a pale yellowish brown or pale reddish brown ginseng obtained by steaming and drying 6-year-old fresh ginseng roots without peeling off the skin. During a process in which fresh ginseng is steamed and dried by special processing technology in order to prepare red ginseng, physiologically active components beneficial to the human body are produced. Such physiologically active components of red ginseng include anticancer components (ginsenoside RH2; inhibition of cancer cell proliferation and metastasis), cancer cell activity inhibitory components (panaxytriol; inhibition of weight loss in cancer patients); platelet aggregation inhibitory components (maltol; thrombosis inhibitory components), obesity inhibitory components, aging inhibitory components, and components that neutralize heavy metal toxicity.

On the other hand, white ginseng is a ginseng prepared by peeling the skin from 4-6-year-old fresh ginseng roots and drying the peeled ginseng roots to a water content of 14% or less. It is yellowish white in color and is prepared by natural sunlight drying, hot-air drying or other drying methods without steaming, unlike the preparation of red ginseng.

The composition for skin application according to the present invention is characterized in that it contains, as an active ingredient, a polysaccharide extract of red ginseng having a molecular weight of less than 10,000 among polysaccharide extract fractions of red ginseng having various molecular weights. The inventive composition containing as an active ingredient the polysaccharide extract of red ginseng having a molecular weight of less than 10,000 has the effect of increasing the expression of mRNA of mitochondrial electron transport system enzymes in skin keratinocytes, thereby activating the skin cells, enhancing skin elasticity and preventing skin aging. Among polysaccharide extracts of red ginseng, an extract having a molecular weight of less than 10,000 has excellent effects compared to a polysaccharide extract of white ginseng having the same molecular weight.

The composition for skin application according to the present invention contains the polysaccharide extract of red ginseng, which has a molecular weight of less than 10,000, in an amount of 0.1-10 wt % based on the total weight of the composition.

In one embodiment, the composition for skin application according to the present invention can be formulated in the form of beauty compositions which may be, for example, cosmetic compositions. In this case, the inventive composition for skin application contains a cosmetically or dermatologically acceptable medium or base. The composition may be provided in the form of any topically applicable formulations, for example, a solution, a gel, a solid, an anhydrous paste, an oil-in-water emulsion, a suspension, a micro emulsion, a microcapsule, a micro granule, an ionic (liposome) or nonionic vesicular dispersion, a cream, a skin lotion, a milk lotion, a powder, an ointment, a spray or a conceal stick. These compositions can be prepared according to any conventional method known in the art. In addition, the composition according to the present invention may be used in the form of a foam composition or an aerosol composition containing a compressed propellant.

Moreover, the composition for skin application according to the present invention may contain additives commonly used in the cosmetic or dermatological field, for example, fat, an organic solvent, a solubilizing agent, a concentrating agent, a gelling agent, a softener, an antioxidant, a suspending agent, a stabilizer, a foaming agent, an aromatic, a surfactant, water, an ionic or non-ionic emulsifier, a filler, a metal ion sequestering agent, a chelating agent, a preservative, vitamins, a blocking agent, a wetting agent, essential oil, dyes, pigments, a hydrophilic or lipophilic activator, lipid vesicles, or the like. These additives may be included in an amount commonly used in the cosmetic or dermatological field.

The formulation of the composition for skin application according to the present invention is not specifically limited and may be suitably selected according to the intended purpose. Examples of the formulation include, but are not limited to, skin softeners (skin lotion and milk lotion), nourishing lotion, essence, nourishing cream, massage cream, pack, gel, eye cream, eye essence, cleansing cream, cleansing foam, cleansing water, powder, body lotion, body cream, body oil and body essence.

In one embodiment of the present invention, the composition for skin application may be applied to a face, particularly the eye rims, the sides of the mouth, the cheeks, the forehead, the neck, hands and feet, but is not limited thereto.

The composition for skin application according to the present invention may be formulated into a Chinese medicine for supplementing Qi.

In Chinese medicine, Qi is defined as (1) a delicate and fine substance that constitutes the human body, maintains life force or vital energy and is rich in nutritional activity, and (2) the physiological function of organ tissues. The substance of (1) is a fundamental substance for the function of (2), and the function of (2) is exhibited by (1). Qi can be classified according to source into hereditary essential Qi transmitted from parents, acquired Qi obtained by the digestion and absorption of food, and clear Qi resulting from air by breathing. Herein, the food-related Qi can be controlled postnatally, and thus the supplement of Qi can lead to the production of energy by the intake of nutrients. This leads to increases in cellular metabolism and energy production, and this phenomenon can be observed by an increase in mitochondrial activity in cells using dermatological mechanism.

MODE FOR INVENTION

Hereinafter, the present invention will be described in further detail with reference to examples and test examples. It is to be understood, however, that these examples are for illustrative purposes only and are not intended to limit the scope of the present invention and that those skilled in the art will appreciate that various modifications, additions and substitutions are possible, without departing from the scope and spirit of the invention.

EXAMPLE 1

Preparation of Polysaccharide Extracts from Red Ginseng and White Ginseng

Sliced red ginseng and white ginseng were sufficiently dried at 60° C. for 2 days. The dried red ginseng and white ginseng slices had a water content of less than 5%. The dried red ginseng and white ginseng slices were grounded into fine particles using a grinder. In the process of grinding the ginseng slices, the fine particles are preferably maintained at a particle size distribution of about 2-5 mm. Then, the red ginseng and white ginseng fine particles were dispersed in water at a concentration of 15% and then extracted with slow stirring at room temperature for 24 hours. The extracts were centrifuged and then filtered through a 1-μm pore size membrane. The filtrates were concentrated to a volume of ⅒ at about 55° C. Ethanol was added slowly to the concentrates, thereby obtaining purified polysaccharide extracts of red ginseng and white ginseng polysaccharide. Herein, ethanol was added until the concentration of ethanol reached about 85%. Then, the precipitated red ginseng and white ginseng polysaccharides were recovered and dried at 40° C. for 24 hours, thereby obtaining red ginseng and white ginseng polysaccharide powders. Then, each of the polysaccharide powders was fractioned into extracts having molecular weights of less than 10,000, from 10,000 to 30,000, from 30,000 to 100,000, and more than 100,000 by ultrafiltration.

TEST EXAMPLE 1

Control of Expression of Mitochondrial Electron Transport System Enzymes

Step 1: Cell Line and Cell Culture

Human epidermal neonatal keratinocyte cells (purchased from Lonza, Inc., Walkersville, Md., USA) were subcultured in a $CO_2$ incubator under the conditions of 37° C. and 5% $CO_2$ according to the guidance of the manufacturer (Lonza, Inc., Walkersville, Md., USA). Specifically, the cells were cultured in 500 ml of KBM-2 medium (Clonetics CC-3103) using a KGM-2 Bullet kit [containing 2 ml of bovine pituitary extract (BPE), 0.5 ml of human epidermal growth factor (hEGF), 0.5 ml of insulin, 0.5 ml of hydrocortisone, 0.5 ml of transferrin, 0.5 ml of epinephrine and 0.5 ml of GA-1000 (gentamycin sulfate)+amphofericin-B)].

Step 2: Examination of Control of Expression of Mitochondrial Electron Transport System Enzyme Genes The cultured human epidermal neonatal keratinocyte cells were treated with 10 μM of each of the red ginseng and white ginseng polysaccharide extract fractions having various molecular weights, obtained in Example 1. In addition, the cultured cells were treated with 30 μM of coenzyme Q10 as a positive control. Then, the cells were cultured for 48 hours, after which the cells were washed twice with 10 ml of phosphate buffered saline (PBS), and total RNA was isolated from the cells using Trizol reagent (Invitrogen, Carlsbad, Calif., USA).

The isolated RNA was purified using a Qiagen RNeasy kit (Qiagen, Valencia, Calif., USA), and the quality and concentration of the RNA were analyzed using Agilent 2100 Bio-Analyzer (Agilent Technology, Santa Clara, Calif., USA). cDNA was synthesized from the isolated RNA using Superscript Reverse Transcriptase (RT) II kit (Invitrogen) and subjected to real time-reverse transcription polymerase chain reaction (Q-RT-PCR), thereby quantitatively analyzing changes in the expressions of ND5 and ND6 genes (belonging to complex I of mitochondrial electron transport system enzymes) and ATP6 and ATP8 genes (belonging to complex V) in the cells . The changes in the expression patterns of the genes were evaluated using TaqMan gene expression assay kit (Applied Biosystems, Forster City, Calif., USA) on the basis of human glyceraldehyde-3P-dehydrogenase (GAPDH, 4333764F, Applied Biosystems).

Figure 2:
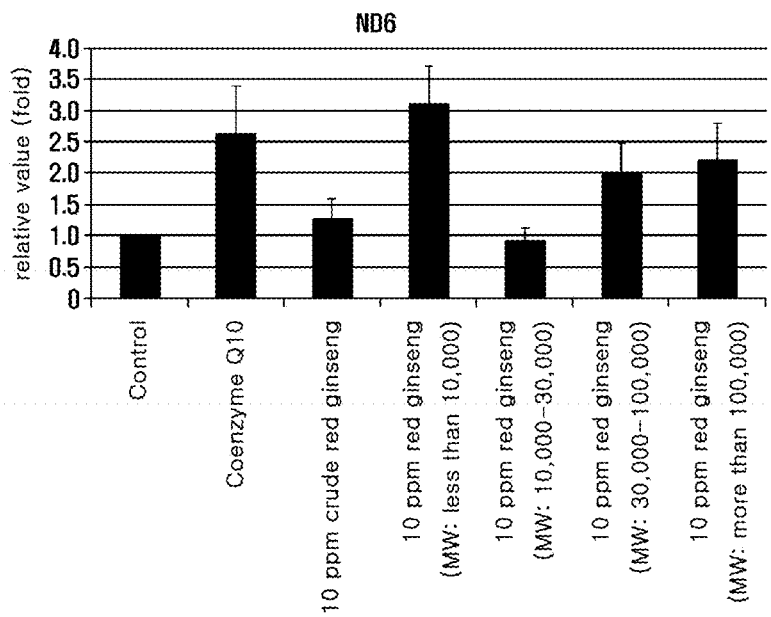
Figure 3:
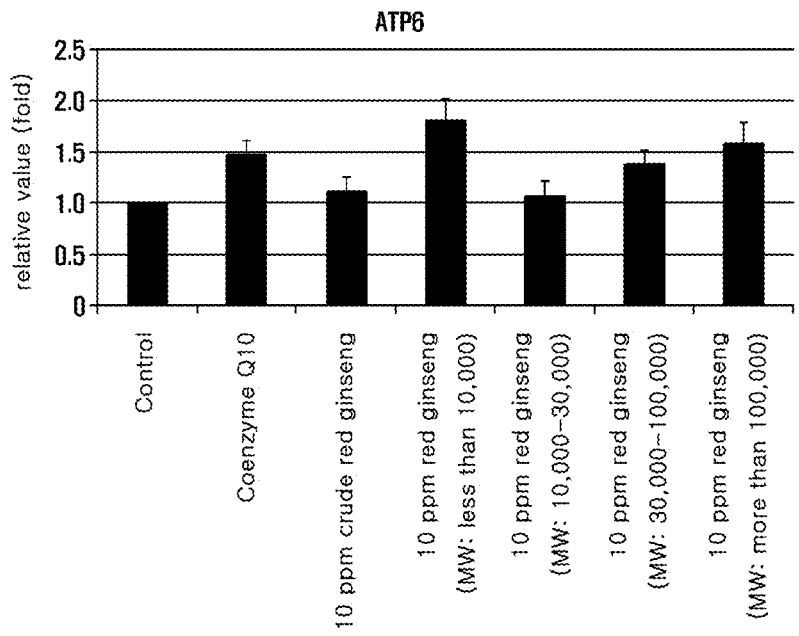
Figure 4:
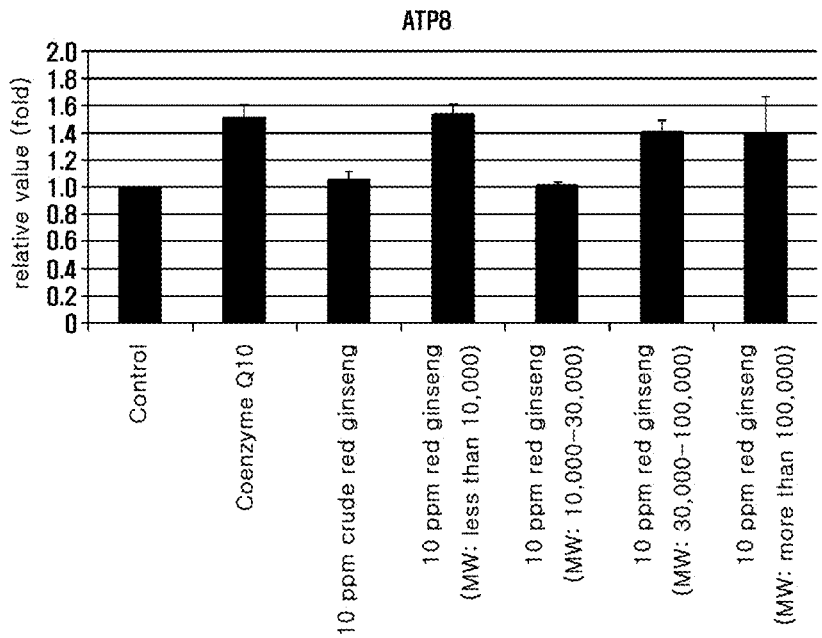

First, the polysaccharide extract of red ginseng was fractioned according to molecular weight, after which the expression levels of the mitochondrial enzymes ND5, ND6, ATP6 and ATP8 in the cells treated with each of the extract fractions was performed by RT-PCR, and the ratios of the expressions of the mitochondrial enzymes relative to those in the control group were measured. The results of the measurement are shown in FIGS. 1 to 4. As a result, it could be seen that the red ginseng polysaccharide extract having a molecular weight of less than 10,000 most significantly increased the expression levels of ND5, ND6, ATP6 and ATP8 and had excellent effects compared to the positive control coenzyme Q10.

The above PCR reaction was performed under the following conditions: 50 cycles of denaturation at 95° C. for 15 sec, annealing at 60° C. for 1 min and extension at 60° C. for 1 min. In addition, the names, accession numbers and sequences of the genes used in the PCR reaction are shown in Table 1 below.

TABLE 1

| Gene name (accession number) | Sequence |
|---|---|
| MT-ND5 (Hs02596878_g1) | 5'-AGCCCTCGCTGTCACTTTCCTAGGA-3' (SEQ ID NO: 1) |
| MT-ND6 (Hs02596879_g1) | 5'-TGAAAGAGTATGATGGGGTGGTGGT-3' (SEQ ID NO: 2) |
| MT-ATP6 (Hs02596862_g1) | 5'-ATTACTGCAGGCCACCTACTCATGC-3' (SEQ ID NO: 3) |
| MT-ATP8 (Hs02596863_g1) | 5'-CGTATGGCCCACCATAATTACCCCC-3' (SEQ ID NO: 4) |

Figure 5:
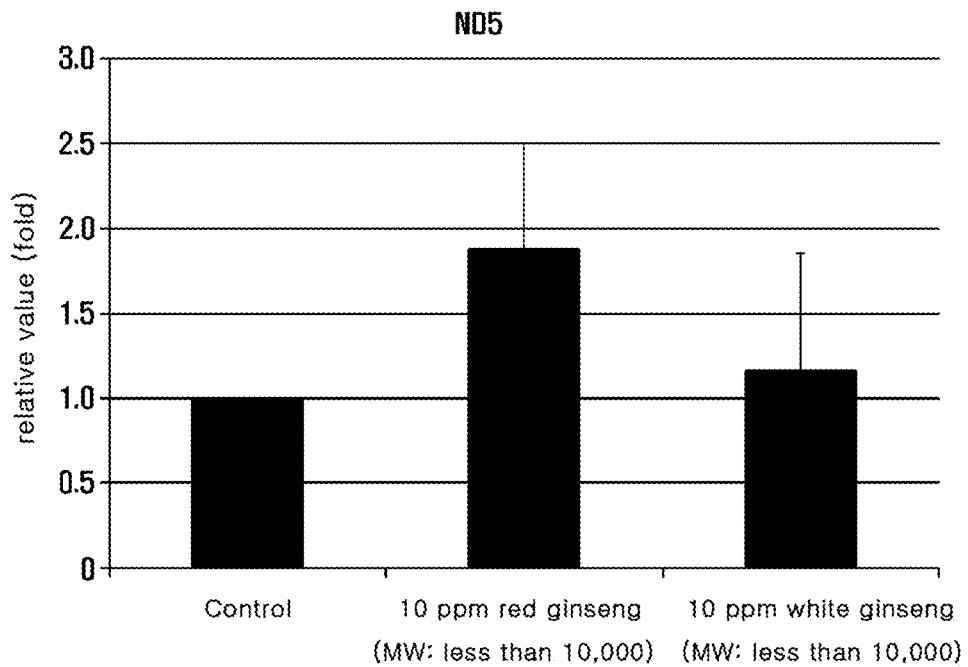
FIGS. 5 to 8 are graphic diagrams showing the results obtained by treating cells with each of a polysaccharide extract of red ginseng and a polysaccharide extract of white ginseng, which have a molecular weight of less than 10,000, and then measuring the expression levels of ND5, ND6, ATP6 and ATP8 in the cells.
Figure 6:
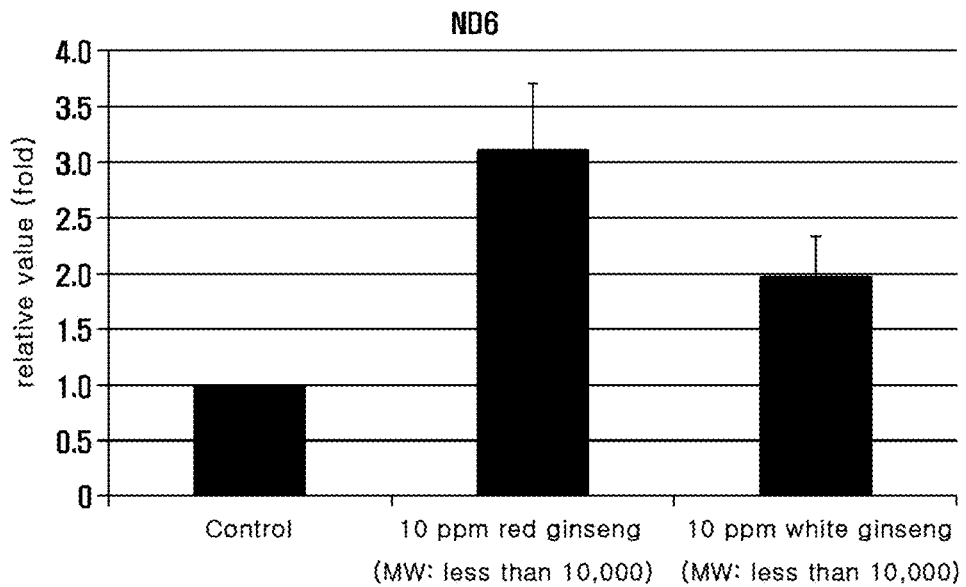
Figure 7:
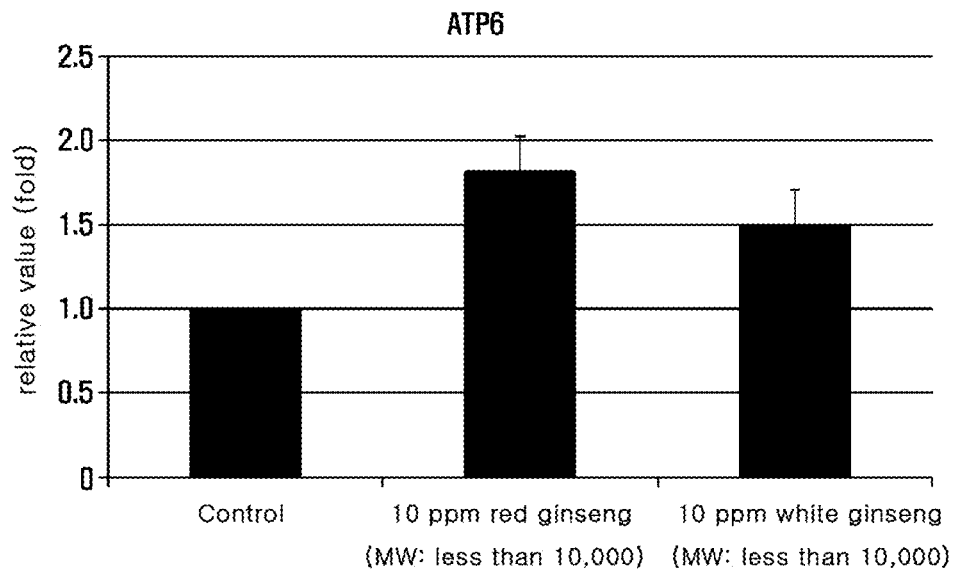
Figure 8:
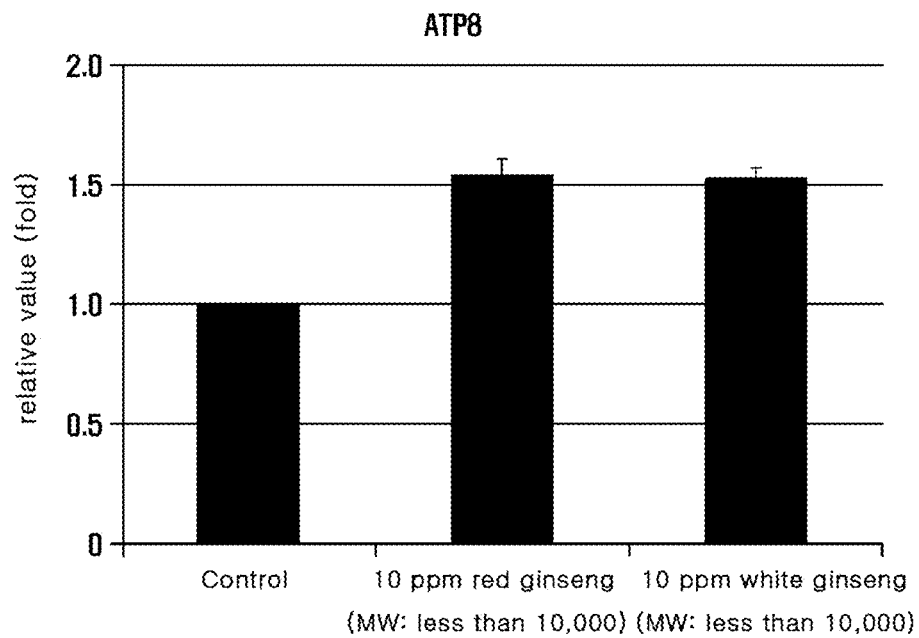

Based on the above results, the expression levels of ND5, ND6, ATP6 and ATP8 in the cells treated with each of the red ginseng and white ginseng polysaccharide extracts having a molecular weight of less than 10,000 were measured by RT-PCR. The results of the measurement are shown in FIGS. 5 to 8. As can be seen therein, the inventive red ginseng polysaccharide extract having a molecular weight of less than 10,000 significantly increased the expression levels of the mitochondrial enzymes compared to the white ginseng polysaccharide extract having the same molecular weight.

FORMULATION EXAMPLE 1

Nourishing Cream

A nourishing cream having the composition shown in Table 2 below was prepared according to a conventional method (unit: wt %).

TABLE 2

| Component | Content |
|---|---|
| Purified water | Balance |
| Glycerin | 3.0 |
| Butylene glycol | 3.0 |
| Liquid paraffin | 7.0 |
| Beta-glucan | 7.0 |
| Carbomer | 0.1 |
| Red ginseng polysaccharide extract having a molecular weight of less than 10,000 | 3.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Preservative | q.s. |
| Fragrance | q.s. |
| Pigment | q.s. |
| Triethanolamine | 0.1 |

FORMULATION EXAMPLE 2

Massage Cream

A massage cream having the composition shown in Table 3 below was prepared according to a conventional method (unit: wt %).

TABLE 3

| Component | Content |
|---|---|
| Purified water | Balance |
| Glycerin | 8.0 |
| Butylene glycol | 4.0 |
| Liquid paraffin | 45.0 |
| Beta-glucan | 7.0 |
| Carbomer | 0.1 |
| Red ginseng polysaccharide extract having a molecular weight of less than 10,000 | 1.0 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Preservative | q.s. |
| Fragrance | q.s. |
| Pigment | q.s. |
| Paraffin | 1.5 |

FORMULATION EXAMPLE 3

Pack

A pack having the composition shown in Table 4 below was prepared according to a conventional method (unit: wt %).

TABLE 4

| Component | Content |
|---|---|
| Purified water | Balance |
| Glycerin | 4.0 |
| Polyvinyl alcohol | 15.0 |
| Hyaluronic acid extract | 5.0 |
| Beta-glucan | 7.0 |
| Alantoin | 0.1 |
| Red ginseng polysaccharide extract having a molecular weight of less than 10,000 | 0.5 |
| Nonyl phenyl ether | 0.4 |
| Polysorbate 60 | 1.2 |
| Preservative | q.s. |
| Fragrance | q.s. |
| Pigment | q.s. |
| Ethanol | 6.0 |

The invention claimed is:

1. A method of using a composition for skin application, which contains, as an active ingredient, a polysaccharide extract of red ginseng fractionated to have molecular weights of less than 10,000; the method comprising applying said composition to skin.

2. The method according to claim 1, wherein application of the composition promotes the expression of mitochondrial electron transport system enzymes in skin cells.

3. The method according to claim 1, wherein application of the composition reduces skin wrinkles.

4. The method according to claim 1, wherein application of the composition enhances skin elasticity.

5. The method according to claim 1, wherein application of the composition prevents skin aging.

6. The method according to claim 1, wherein application of the composition supplements Qi in the human body as a Chinese medicine.

* * * * *